United States Patent
Kandel et al.

(10) Patent No.: US 11,926,605 B2
(45) Date of Patent: Mar. 12, 2024

(54) FUNCTIONALIZED BIFURAN AND SYNTHESIS THEREOF

(71) Applicant: ExxonMobil Chemical Patents Inc., Baytown, TX (US)

(72) Inventors: Kapil Kandel, Humble, TX (US); Stephen T. Cohn, Spring, TX (US); Michael Salciccioli, Ann Arbor, MI (US); Crisita Carmen H. Atienza, Houston, TX (US); Alan A. Galuska, Huffman, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 801 days.

(21) Appl. No.: 16/978,496

(22) PCT Filed: Feb. 11, 2019

(86) PCT No.: PCT/US2019/017461
§ 371 (c)(1),
(2) Date: Sep. 4, 2020

(87) PCT Pub. No.: WO2019/182693
PCT Pub. Date: Sep. 26, 2019

(65) Prior Publication Data
US 2021/0009545 A1 Jan. 14, 2021

Related U.S. Application Data

(60) Provisional application No. 62/645,846, filed on Mar. 21, 2018.

(51) Int. Cl.
*C07D 307/36* (2006.01)
*C07D 307/54* (2006.01)
*C08G 63/185* (2006.01)

(52) U.S. Cl.
CPC ......... *C07D 307/36* (2013.01); *C07D 307/54* (2013.01); *C08G 63/185* (2013.01)

(58) Field of Classification Search
USPC ........................................................ 528/234
See application file for complete search history.

(56) References Cited

U.S. PATENT DOCUMENTS

| | | | |
|---|---|---|---|
| 4,025,492 A | 5/1977 | Binsack et al. | 260/75 |
| 4,093,603 A | 6/1978 | Jackson, Jr. et al. | 260/75 |
| 4,136,089 A | 1/1979 | Bier et al. | 528/309 |
| 4,176,224 A | 11/1979 | Bier et al. | 528/309 |
| 4,208,527 A | 6/1980 | Horlbeck et al. | 528/279 |
| 4,238,593 A | 12/1980 | Duh | 528/272 |
| 5,681,918 A | 10/1997 | Adams et al. | 528/279 |

FOREIGN PATENT DOCUMENTS

| | | | |
|---|---|---|---|
| EP | 1726589 A2 * | 11/2006 | ........... C07D 307/54 |
| WO | WO2015/112252 | 7/2015 | ............. C07C 15/14 |
| WO | WO2019/199461 | 10/2019 | ............. C07C 1/247 |

OTHER PUBLICATIONS

Naoki Miyagawa et al: "Preparation of Furan Polymer-based Biopolyester Showing High Melting Points", Chemistry Letters, vol. 46, No. 10, Oct. 5, 2017 (Oct. 5, 2017), pp. 1505-7598; (Year: 2017).*
Tuomo P. Kainulainen et al: UV-Blocking Synthetic Biopolymer from Biomass-based bifuran Diester and Ethylene Glycol (Year: 2018).*
Juwaini, N. et al. (2012) "Catalytic Regioselective Oxidative Coupling of Furan-2-Carbonyls with Simple Arenes," *ACS Catal.*, v.2(8), pp. 1787-1791.
Kainulainen, Tuomo P. et al. (2018) "UV-Blocking Synthetic Biopolymer from Biomass-Based Bifuran Diester and Ethylene Glycol," *Macromolecules*, v.51(5), pp. 1822-1829.
Kozhevnikov, I.V. (1976) "Oxidative Coupling of Furan Derivatives to Bifurans Catalyzed by Palladium(II)," *React. Kinet. Catal. Lett.*, v.5(4), pp. 415-419.
Li, T. et al. (1997) "Montmorillonite Clay Catalysis. Part 2.1 An Efficient and Convenient Procedure for the Preparation of Acetals catalysed by Montmorillonite K-10," *J. Chem. Research (S)*, Issue 1, pp. 26-27.
Li, N. & Wang, Y. et al. (2014) "Palladium-Catalyzed C—H Homocoupling of Furans and Thiophenes Using Oxygen as the Oxidant," *Org. Lett.*, v.16(10), pp. 2732-2735.
Miyagawa, Naoki et al. (2017) "Preparation of Furan Dimer-based Biopolyester Showing High Melting Points," *Chemistry Letters*, v.46(10), pp. 1535-1538.
Oikawa, Y. et al. (1982) "Protection of hydroxy groups by intramolecular oxidative formation of methoxybenzylidene acetals with DDQ," *Tetrahedron Lett.*, v.23(8), pp. 889-892.
Patel, B. & Gopinath, R. et al. (2002) "$V_2O_5$—$H_2O_2$: a Convenient Reagent for the Direct Oxidation of Acetals to Esters," *Tetrahedron Lett.*, v.43(29), pp. 5123-5126.

(Continued)

*Primary Examiner* — Terressa Boykin

(57) ABSTRACT

A 5,5'-Di-(protected)-2,2'-bifuran:

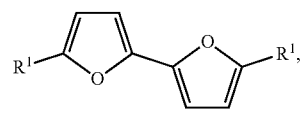

wherein each $R^1$ is independently an unsubstituted or substituted 5- or 6-member 1,3-dioxo-2-yl ring radical. Processes for making the bifuran include coupling 2-(protected)-furfural. Processes for using the bifuran include deprotection, functionalization, and/or polymerization to form a polyester. The polyester can be a renewable, high-performing polyester offering a combination of low cost of production, high sustainability, and excellent performance.

24 Claims, No Drawings

(56) References Cited

OTHER PUBLICATIONS

Yasukawa et. al. (2016) "Palladium on Carbon-Catalyzed Chemoselective Oxygen Oxidation of Aromatic Acetals," *Org. Lett.*, v.18(21), pp. 5604-5607.

* cited by examiner

FUNCTIONALIZED BIFURAN AND SYNTHESIS THEREOF

CROSS-REFERENCE TO RELATED APPLICATIONS

This application is a National Phase Application claiming priority to PCT Application Serial No. PCT/US2019/017461 filed Feb. 11, 2019, which claims the benefit of Provisional Application No. 62/645,846, filed Mar. 21, 2018, the disclosures of which are incorporated herein by reference.

FIELD

This disclosure relates to bifuran, derivatives thereof, polymers comprising structural components of bifuran and/or derivatives thereof, and processes for making the same.

BACKGROUND

Renewable, high-performing polyesters, have the potential to disrupt the industry if they can offer a combination of lower cost of production, higher sustainability, and better performance in application. Currently, bio-based products suffer from several issues ranging from reduced applied properties, high cost, or limited availability due to logistical issues surrounding feedstock. Furthermore, current renewable or fractionally-renewable products produced from corn ethanol-derived ethylene incur an inefficient number of process steps that are much more expensive than the petroleum-derived conventional polyesters. Additionally, many sugar-derived materials or monomers compete with land with food sources necessary to sustain the global population. To satisfy all three targets, cost, sustainability, product properties, with a single material, new monomers should be used that incorporate oxygen and carbon structures that match the cellulose or hemi-cellulose feed source. One such building block can be functionalized bifuran monomers synthesized from the coupling of furans derived from hemi-cellulose.

As disclosed in Li et al. in 16 *Org. Lett.* 2732-2735 (2014); Juwaini et al. in 2 *ACS. Catal.* 1787-1791 (2012); the initial step during oxidative coupling of furan species with palladium catalyst is electrophilic palladation as shown in Scheme 1 for methyl furan.

However, carbonyl-containing functionalized derivatives of furan with 2-substitution such as —CHO, —COOCH$_3$, —COOC$_2$H$_5$, —CH(OOCCH$_3$)$_2$) are known to make the C-5 carbon less electron rich and reduce its activity in the electrophilic palladation step, slowing down the coupling reaction. See Kozhevnikov, I. V., in 5 *React. Kinet. Catal. Lett.* 415 (1976) ([https://]doi.org/10.1007/BF02060888). The industry thus has a need for a new chemistry route to couple functionalized furan molecules that can offer greater flexibility in products, and/or improve process economics via reaction step-skipping.

Scheme 1

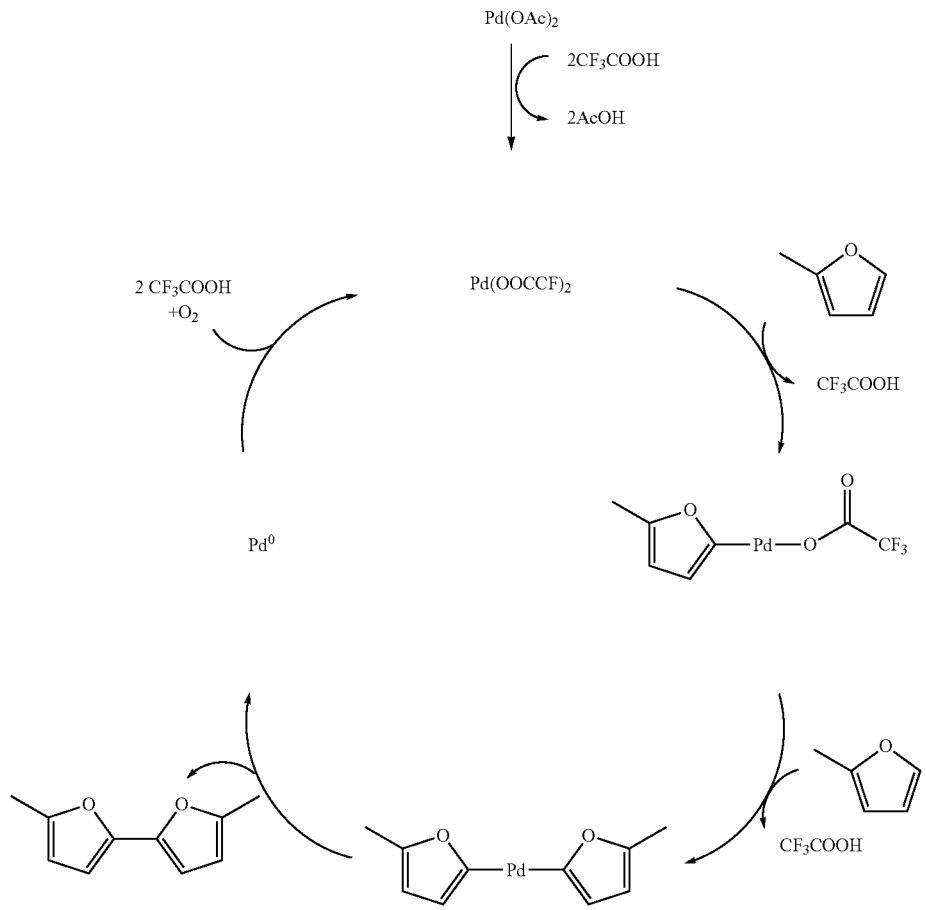

SUMMARY

This summary introduces a selection of concepts that are further described below in the detailed description. This summary is not intended to identify key or essential features of the claimed subject matter, nor is it intended to be used as an aid in limiting the scope of the claimed subject matter.

In one aspect of the invention, a composition of matter comprises (or consists of, or consists essentially of) 5,5'-di-(protected)-2,2'-bifuran having the Formula (F-I) or preferably Formula (F-II), wherein Formula (F-I) is:

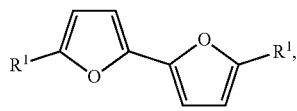
(F-I)

wherein each R is independently a 5- or 6-member 1,3-dioxo-2-yl ring radical, which may optionally be substituted with one or more substituents preferably comprising alkyl radical(s) having from 2 to 12 carbon atoms, more preferably each R' is 1,3-dioxolan-2-yl or 1,3-dioxan-2-yl; and wherein Formula (F-II) is:

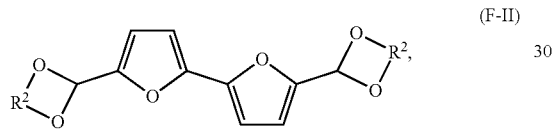
(F-II)

wherein each $R^2$ is independently alkylene of from 2 to 12 carbon atoms; preferably ethylene or propylene, or substituted ethylene or 1,3-propylene wherein the substituents are preferably selected from alkyls of 1 to 10 carbon atoms; more preferably each $R^2$ is, independently ethylene, 1,2-propylene, or 1,3-propylene; more preferably ethylene, i.e., wherein the 5,5'-di-(protectant)-2,2'-bifuran is 5,5'-di-(1,3-dioxolan-2-yl)-2,2'-bifuran. The di-protected bifuran of Formula (F-I) has utility as a stabilized raw material for the synthesis of bifuran derivatives, including biodegradable materials. The diacetal bifuran of Formula (F-II) has utility in the synthesis of bifuran derivatives, including (2,2'-bifuran)-5,5'-dicarboxylate esters and polyesters.

In another aspect of the invention, a chemical process couples a protected furfural compound to form 5,5'-di-(substituted)-2,2'-bifuran. Unlike the carbonyl group in furfural, the protected group does not take part in the resonance of the furan ring, and therefore the electron density at the C-5 carbon is higher, which can facilitate the coupling process. The process can start with 2-(protected)-furan and/or its preparation, e.g., with 2-acetal-bifuran and/or by protecting the aldehyde functionality in furfural. The process can also include, as desired, deprotecting, functionalizing, polymerizing, and/or otherwise derivatizing the bifuran, and so on.

In another aspect of the invention, the 5,5'-di-(protected)-2,2'-bifuran is polymerized in one or more steps, optionally including formation of one or more intermediate 5,5'-di-(substituted)-2,2'-bifurans, to form a polyester, e.g., comprising (2,2'-bifuran)-5,5'-dicarboxylate. Preferably the polyester comprises poly(alkylene glycol (2,2'-bifuran)-5,5'-dicarboxylate), more preferably poly(ethylene glycol (2,2'-bifuran)-5,5'-dicarboxylate).

DETAILED DESCRIPTION

Throughout the entire specification, including the claims, the following terms shall have the indicated meanings.

The term "and/or" refers to both the inclusive "and" case and the exclusive "or" case. Such term is used herein for brevity. For example, a composition comprising "A and/or B" may comprise A alone, B alone, or both A and B.

Numbering is according to IUPAC, e.g., for furan:

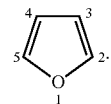

Furfural may also be referred to herein as furan-2-carbaldehyde, fural, furfuraldehyde, or 2-furaldehyde.

Furfural ethylene glycol acetal may also be referred to herein as 2-(2-furyl)-1,3-dioxolane or 2-furfural ethylene glycol acetal.

2-Furoic acid may also be referred to herein as furan-2-carboxylic acid.

Acetal has the formula:

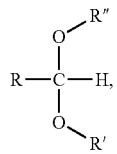

wherein R, R', and R" are organic fragments and R' and R" may join together to form a 1,3-dioxo ring structure.

A furan coupling process refers to a process having at least one step involving coupling of furan or a furan derivative, and may optionally include steps preceding or subsequent to the coupling step, e.g., preparing the furan derivative, deprotecting the coupled furan derivative, polymerizing the bifuran, and so on.

Protecting refers to the introduction of a protecting group into a molecule by chemical modification of a functional group to obtain chemoselectivity in subsequent reaction(s). A protected molecule refers to the molecule having the chemically modified functional group that is formed by the protection. The protectant refers to the reagent(s) used in the chemical modification of the functional group. Deprotecting refers to the removal of the protective group from the chemically modified functional group, or other or further modification of the chemically modified functional group that reduces the chemoselectivity.

Room temperature is 25° C. and atmospheric pressure is 101.325 kPa unless otherwise noted.

The term "consisting essentially of" in reference to a composition is understood to mean that the composition can include additional compounds or substituents other than those specified, in such amounts to the extent that they do not substantially interfere with the essential function of the composition, or if no essential function is indicated, in any amount up to 5 percent by weight of the composition.

As used herein, the prefixes di- and tri- generally refer to two and three, respectively, with the exception of diacid and diol components noted herein. Similarly, the prefix "poly-" generally refers to two or more, and the prefix "multi-" to three or more.

For purposes herein a "polymer" refers to a compound having two or more structural units (see below for polyester structural units), that is, a degree of polymerization of two or more, where the structural units can be of the same or different species. A "homopolymer" is a polymer having structural units or residues that are the same species. A "copolymer" is a polymer having two or more different species of structural units or residues. "Different" in reference to structural unit species indicates that the structural units differ from each other by at least one atom or are different isomerically. Unless otherwise indicated, reference to a polymer herein includes a copolymer, a terpolymer, or any polymer comprising a plurality of the same or different species of repeating units.

The term "polyester", as used herein, refers to a polymer comprised of residues derived from one or more polyfunctional acid moieties, collectively referred to herein as the "diacid component," in ester linkage with residues derived from one or more polyhydroxyl compounds, which may also be referred to herein as "polyhydroxyls" or "polyols" and collectively as the "diol component." The term "repeating unit," also referred to as the structural units, as used herein with reference to polyesters refers to an organic structure having a diacid component residue and a diol component residue bonded through a carbonyloxy group, i.e., an ester linkage. Reference to the equivalent terms "copolyesters" or "(co)polyesters" or "polyester copolymers" herein is to be understood to mean a polymer prepared by the reaction of two or more different diacid compounds or ester producing equivalents thereof that incorporate different diacid residues into the backbone, and/or two or more different diol compounds that incorporate different diol residues into the backbone, i.e., either one or both of the diacid and diol components incorporate a combination of different species into the polymer backbone. A polyester homopolymer refers to a polyester having single species of diacid and diol compounds.

The carboxylic acids and/or esters used to make the polyesters, or the residues of which are present therein, are collectively referred to herein as the "diacid component", including both difunctional and multifunctional species thereof, or simply as the "acid component," which is intended to include polycarboxylic acids and any derivative of a polycarboxylic acid, including its associated acid halides, esters, half-esters, salts, half-salts, anhydrides, mixed anhydrides, or mixtures thereof, capable of forming esters useful in a reaction process with a diol to make polyesters. The hydroxyl compounds used to make the polyesters, or the residues which are present therein, are collectively referred to herein as the "diol component," including both difunctional and multifunctional species thereof, or simply as the hydroxyl or polyol component. The polyhydroxy compounds disclosed herein may be used in the diol component in any combination. The polyesters may also be prepared from esters comprising a diol residue and a diacid residue, e.g., (HO)—R—C(O)O—R'—C(O)OH where R and R' are organic fragments.

The term "residue," as used herein, means the organic structure of the monomer in its as-polymerized form as incorporated into a polymer, e.g., through a polycondensation and/or an esterification or transesterification reaction from the corresponding monomer. Throughout the specification and claims, reference to the monomer(s) in the polymer is understood to mean the corresponding as-polymerized form or residue of the respective monomer. For purposes herein, it is to be understood that by reference to a polyester comprising a diacid component and a diol component, the diacid and diol components are present in the polymer in the as-polymerized (as-condensed) form. For example, the diacid component is present in the polymer as dicarboxylate in alternating ester linkage with the diol component, yet the polyester may be described as being comprised of, for example, the dicarboxylic acid alkyl ester and diol, where it is understood the alkyl ester groups in the starting material are not present in the polyester. For example, the diacid component is present in the polymer in alternating ester linkage with the diol component, yet the polyester may be described as being comprised of, for example, the dicarboxylic acid or dicarboxylic acid alkyl ester and diol, e.g., terephthalic acid-ethylene glycol polyester or dimethyl terephthalate-ethylene glycol polyester, where it is understood the methyl ester groups in the starting material(s) are not generally present in the polyester, but may be present in minor or trivial amounts, e.g., as esters on the ends of some of the polymer chains.

The percentages of monomers are expressed herein as mole percent (mol %) based on the total moles of monomers present in the reference polymer or polymers component. All other percentages are expressed as weight percent (wt %), based on the total weight of the particular composition present, unless otherwise noted. Mole percentages of the diacid and diol components are expressed herein based on the total moles of the respective component, i.e., the copolyesters comprise 100 mole percent of the polyfunctional acid component and 100 mole percent of the polyfunctional hydroxyl component. Mole percentages of a branching agent are based on the total moles of repeating (ester-linked diacid-diol) units. The molar ratio of the diacid to diol components is preferably around 1.0, especially where high molecular weight is desired, but can be more or less than 1.0 if the polyester comprises homopolymer of the diacid or diol components, e.g., at the ends of the polyester chains.

As used herein, "polycondensation" refers to the formation of a polymer by the linking together of molecules of one or more monomers with the subsequent releasing of water, or a similarly small molecule. Acidolysis polycondensation refers to a unique form of polycondensation in which a polycarboxylic acid in the free acid form is reacted with a poly-hydroxy compound or a derivative thereof, to form the resultant polyester linkages with the subsequent release of water or other leaving group. Acidolysis polycondensation also includes the reaction of a polycarboxylic acid in the free acid form with a polyhydroxy compound comprising a plurality of esterified phenolic substituents, e.g., hydroquinone dialkanoate (e.g., hydroquinone diacetate) with the subsequent formation of the phenol esterification acid; the esterified polyphenol is utilized as the polyhydroxy compound.

As used herein, acids include Brøsted and Lewis acids. A Brønsted acid is any chemical species (atom, ion, molecule, compound, complex, etc.), without limitation, that can donate or transfer one or more protons to another chemical species; and a Brønsted base is any chemical species that can accept a proton from another chemical species. A Lewis acid is any chemical species that is an electron-pair acceptor, and a Lewis base is any chemical species that is an electron-pair donor. An Arrhenius acid is an acid that forms the hydronium ion in an aqueous medium. Some chemical species, such as, for example, vanadium pentoxide ($V_2O_5$), may have both Lewis and Brønsted acidity.

Representative examples of Brønsted acids include mineral acids, organic acids, heteropolyacids, zeolites, and the like. Some representative examples of Lewis acids include compounds of transition metals, lanthanoid metals, and metals and metalloids from Group 4, 5, 13, 14, and 15 of the periodic table of the elements, such as AlCl$_3$, (alkyl)AlCl$_2$, (C$_2$H$_5$)$_2$AlCl, (C$_2$H$_5$)$_3$Al$_2$Cl$_3$, BF$_3$, SnCl$_4$ and TiCl$_4$.

The following abbreviations are used herein: DDQ is 2,3-dichloro-5,6-dicyano-1,4-benzoquinone; Et is ethylene; EG is ethylene glycol; FDCA is furandicarboxylic acid; NPG is 2,2-dimethyl-1,3-propanediol (neopentyl glycol); Pd/C is palladium on carbon.

A composition of matter according to the present invention comprises 5,5'-di-(protected)-2,2'-bifuran, preferably having the Formula (F-I), more preferably the Formula (F-II), wherein Formula (F-I) is:

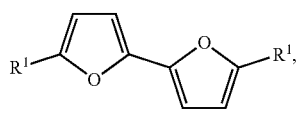

(F-I)

wherein each R$^1$ is independently a 5- or 6-member 1,3-dioxo ring radical, which may optionally be substituted with one or more substituents preferably comprising alkyl radical(s) having from 1 to 12 carbon atoms, more preferably each IV is 1,3-dioxolan-2-yl or 1,3-dioxan-2-yl; and wherein Formula (F-II) is:

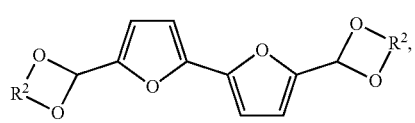

(F-II)

wherein each R$^2$ is independently alkylene of from 2 to 12 carbon atoms; preferably 1,2-ethylene or 1,3-propylene, or substituted 1,2-ethylene or 1,3-propylene, wherein the substituents are selected from alkyls having from 1 to 10 carbon atoms; more preferably each R$^2$ is, independently 1,2-ethylene, 1,2-propylene, or 1,3-propylene; more preferably 1,2-ethylene, i.e., wherein the 5,5'-di-(protected)-2,2'-bifuran is 5,5'-di-(1,3-dioxolan-2-yl)-2,2'-bifuran.

A furan coupling process according to the present invention comprises coupling a protected 2-furaldehyde to form a 5,5'-di-(protected)-2,2'-bifuran. Suitable analogous bifuran coupling procedures and techniques are known from, for example, the Li et al. in *Org. Lett.* (2014), Juwaini, and Kozhevnikov articles mentioned above, except that in the present process protection of the aldehyde or other functional group allows the coupling to proceed at a faster kinetic rate and/or with improved conversion relative to the corresponding furfuraldehyde or other functionalized furan per se. The coupling preferably comprises oxidative addition, metalation, and reductive elimination, optionally in the presence of an oxidant and/or a catalyst. Suitable coupling includes palladation, preferably electrophilic palladation, e.g., in the presence of an oxidant, preferably oxygen and a palladium catalyst, preferably a palladium (II) catalyst such as PdCl$_2$, PdBr$_2$, PdO, Pd(CN)$_2$, Pd(NO$_3$)$_2$, Pd(II) carboxylate salts, more preferably Pd(II) halocarboxylate salts, or more preferably palladium (II) acetate (Pd(OAc)$_2$) and/or palladium (II) trifluoroacetate (Pd(OOCCF$_3$)$_2$), or any combination thereof.

The process can include protecting 2-furaldehyde to form the protected 2-furaldehyde, e.g., wherein the 2-furaldehyde is protected with an alkylene diol to form a 2-furfural alkylene diol acetal. The alkylene diol preferably has from 2 to 12 carbon atoms, more preferably the alkylene diol comprises ethylene glycol, propylene glycol, or propylene-1,3-diol, or substituted ethylene glycol, propylene glycol, or propylene-1,3-diol, wherein the substituents are selected from 1 to 10 carbon alkyls; more preferably the alkylene diol comprises ethylene glycol, propylene-1,2-diol, or propylene-1,3-diol; more preferably ethylene glycol, i.e., wherein the 5,5'-di-(protectant)-2,2$^9$-bifuran is 5,5'-di-(1,3-dioxolan-2-yl)-2,2'-bifuran.

The furaldehyde is preferably protected by contacting the furaldehyde and the diol under suitable reaction conditions, optionally including the removal of water, such as those reported for the reaction of furaldehyde and ethylene glycol in Li et al., *J. Chem. Research (S)*, 26-27 (1997). The protection is preferably in the presence of a catalyst, optionally in the presence of a solvent, preferably toluene, and preferably with the removal of water. Suitable catalysts include Brønsted acids, Lewis acids, or a combination thereof, such as, for example, V$_2$O$_5$, AlCl$_3$, (alkyl)AlCl$_2$, (C$_2$H$_5$)$_2$AlCl, (C$_2$H$_5$)$_3$Al$_2$Cl$_3$, BF$_3$, SnCl$_4$, TiCL$_f$, and the like. Suitable catalysts for the furaldehyde protection reaction preferably include an inorganic oxide, preferably an oxide of metals and metalloids from Group 14, 13, 4, and 2 of the periodic table of the elements, for example, silicon, aluminum, magnesium, and/or zirconium oxides, preferably a silicate, more preferably phyllosilicate, more preferably a clay mineral, more preferably montmorillonite, more preferably montmorillonite K-10, preferably with water removal, and optionally in the presence of a solvent, preferably toluene.

The process may further comprise deprotecting the 5,5'-di(protected)-2,2'-bifuran to form, for example, (2,2'-bifuran)-5,5'-dic arb aldehyde. E.g., the 5,5'-di(protected)-2,2-bifuran may comprise 5,5'-di(alkylene diol acetal)-2,2'-bifuran, preferably 5,5'-di(ethylene glycol acetal)-2,2'-bifuran. The deprotecting may comprise contacting the 5,5'-di(protected)-2,2'-bifuran with a catalyst, preferably a Brønsted and/or Lewis acid. Since deprotection and protection may be equilibrium mediated reactions, the protection catalysts mentioned above may also be suitable for deprotection under conditions more favorable to the deprotected species, i.e., Brønsted acids, Lewis acids, or a combination thereof, such as, for example, V$_2$O$_5$, AlCl$_3$, (alkyl)AlCl$_2$, (C$_2$H$_5$)$_2$AlCl, (C$_2$H$_5$)$_3$Al$_2$Cl$_3$, BF$_3$, SnCl$_4$, TiCl$_4$, and the like. Suitable catalysts for the deprotection reaction include inorganic oxides such as oxides of the Group 14, 13, 4, and 2 metals and metalloids, for example, silicon, aluminum, magnesium, and/or zirconium oxides, preferably a silicate, more preferably phyllosilicate, more preferably a clay mineral, more preferably montmorillonite, more preferably montmorillonite K-10, preferably in the presence of water, and optionally in the presence of a solvent, preferably toluene. Preferably, deprotection is carried out in an acidic aqueous medium, preferably aqueous HCl.

The process may further comprise: reacting the 5,5'-di (protected)-2,2'-bifuran and forming at least one intermediate, preferably wherein the at least one intermediate comprises a 5,5'-di-(substituted)-2,2$^9$-bifuran wherein the 5,5' substituents comprise hydroxyl groups, carboxylic acid groups, ester producing equivalents thereof (preferably the corresponding ester(s), anhydride(s), salts, or acid halide(s) thereof), or a combination thereof; optionally recovering the intermediate(s); and polymerizing an ultimate one of the intermediate(s), preferably by contacting the 5,5'-di-(substituted)-2,2'-bifuran with a functionalized compound comprising two or more ester-forming functional groups, to form a polyester, preferably wherein the hydrocarbyl comprises an alkylene group or a heterocylic group such as an oxo ring, preferably an unsaturated oxo ring, more preferably furanyl or pyranyl.

A polymerization process according to the present invention may comprise polymerizing the 5,5'-di(protected)-2,2'-bifuran in one or more steps, optionally including formation of one or more intermediate 5,5'-di-(substituted)-2,2'-bifurans, to form a polyester comprising (2,2'-bifuran)-5,5'-dicarboxylate, preferably wherein the polyester comprises poly(alkylene glycol (2,2'-bifuran)-5,5'-dicarboxylate), more preferably poly(ethylene glycol (2,2 '-bifuran)-5,5'-dicarboxylate). The polymerization process generally comprises polycondensation of a diacid component and a diol component, e.g., by transesterification, acid catalyzed polymerization, or the like, wherein either or both diacid and diol components comprise the 5,5'-di(protected)-2,2'-bifuran per se and/or a derivative thereof. When a derivative of the precursor 5,5'-di(protected)-2,2'-bifuran is formed as an intermediate, it may be formed in situ in the polymerization reactor, or in a preliminary derivatization reaction in the same or different reactor.

The ultimate intermediate is preferably according to the Formula (F-III):

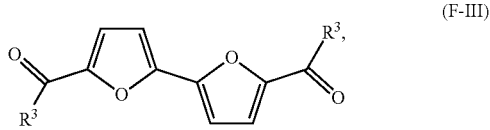

wherein each R³ is independently hydrogen, hydroxyalkyl, carboxyalkyl, halide, OR', or a combination thereof, or wherein the ultimate intermediate is an anhydride thereof; where R' (if present) is hydrogen, hydrocarbyl, hydroxylkyl, carboxyalkyl, or a combination thereof; preferably wherein R and R' (if present) have a number of carbon atoms equal to or less than 20, more preferably equal to or less than 10, more preferably from 1 to 4 carbon atoms, more preferably where R' is methyl.

The process may further comprise: protecting 2-furaldehyde with alkylene diol, preferably ethylene glycol, to form 2-furfural alkylene diol acetal; wherein forming the at least one intermediate comprises forming the alkylene diol; and optionally recycling the alkylene diol from the at least one intermediate formation step to the 2-furaldehyde protection step.

Preferably, a first one of the intermediates comprises (2,2'-bifuran)-5,5'-dicarbaldehyde. The process may further comprise converting the (2,2'-bifuran)-5,5'-dicarbaldehyde to (2,2'-bifuran)-5,5'-dicarboxylic acid or dialkyl (2,2'-bifuran)-5,5'-dicarboxylate (preferably dimethyl (2,2'-bifuran)-5,5'-dicarboxylate), or a combination thereof. The conversion can be effected, for example: by heating the (2,2'-bifuran)-5,5'-dicarbaldehyde in the presence of an oxidant, preferably oxygen, preferably to a temperature of 100-200° C., preferably in a solvent (preferably acetic acid), preferably at an absolute pressure from 1 to 60 bars (100 to 6,000 kilopascal), preferably wherein the 5,5'-di-(substituted)-2,2'-bifuran comprises (2,2'-bifuran)-5,5'-dicarboxylic acid; or by contacting the (2,2'-bifuran)-5,5'-dicarbaldehyde in the presence of an oxidant, preferably oxygen with a metal or metalloid catalyst, preferably Pd, Pb, Mg, or a combination thereof, preferably at a temperature from 40 to 160° C. (more preferably around 80° C. ±5, 10, or 15° C.), preferably at an absolute pressure from 1 to 20 bars (100 to 2,000 kilopascal) (more preferably around 5 bars ±1 or 2 bars (500 kilopascal ±100 or 200 kilopascal)), preferably wherein the 5,5'-di-(substituted)-2,2'-bifuran comprises dialkyl (2,2'-bifuran)-5,5'-dicarboxylate, preferably dimethyl (2,2'-bifuran)-5,5'-dicarboxylate.

In any embodiment of the process, the ultimate intermediate 5,5'-di-(substituted)-2,2'-bifuran preferably has the Formula (F-IV):

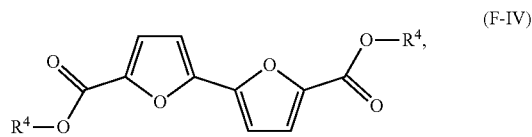

wherein each R⁴ is hydrogen, hydrocarbyl, hydroxyalkyl, carboxyalkyl, or a combination thereof, or wherein the ultimate intermediate is an anhydride thereof, preferably wherein each R⁴ has a number of carbon atoms equal to or less than 20, more preferably equal to or less than 10, more preferably where each R⁴ is hydrogen, methyl, hydroxyethyl, or a combination thereof.

In any embodiment of the process, the 5,5'-di(protected)-2,2'-bifuran preferably comprises 5,5'-di-(alkylene diol acetal)-2,2'-bifuran, and formation of the intermediate preferably comprises contacting the 5,5'-di-(alkylene diol acetal)-2,2'-bifuran with vanadium (V) oxide and peroxide, preferably hydrogen peroxide, preferably at a temperature less than 20° C., preferably at 0-15° C., preferably in an alcoholic medium, more preferably in methanol, and wherein R is alkyl, preferably methyl.

In any embodiment of the process, the 5,5'-substituents of the ultimate intermediate 2,2'-bifuran preferably comprise carboxylic acid groups or ester producing equivalents thereof, preferably the corresponding acid halide(s), ester(s), salts, or anhydride(s) thereof, preferably the 5,5'-di-(substituted)-2,2'-bifuran compound comprises (2,2'-bifuran)-5,5'-dicarboxylic acid, dialkyl (2,2'-bifuran)-5,5'-dicarboxylate (preferably dimethyl (2,2'-bifuran)-5,5'-dicarboxylate), or a combination thereof; and the polymerization preferably comprises contacting the ultimate intermediate with the functionalized compound and forming the polyester, wherein the functionalized compound comprises two or more hydroxyl groups, preferably alkylene diol, more preferably ethylene glycol.

According to any embodiment of the process, the 5,5'-di (protected)-2,2'-bifuran comprises 5,5'-di-(alkylene diol acetal)-2,2'-bifuran, and formation of the intermediate comprises contacting the 5,5'-di-(alkylene diol acetal)-2,2'-bifuran with palladium on carbon catalyst, preferably 5 mole percent Pd on carbon, in the presence of an oxidant, preferably oxygen, preferably at a temperature from 40 to 160° C., preferably at 80° C. ±20° C., preferably in a glycolic medium, more preferably in ethylene glycol, to form bis(2-hydroxyalkyl) (2,2'-bifuran)-5,5 '-dicarboxylate, preferably bis(2-hydroxyethyl) (2,2'-bifuran)-5,5'-dicarboxylate.

According to any embodiment of the process, the functionalized compound preferably comprises two or more carboxylic acid groups or ester producing equivalents thereof, preferably the corresponding acid halide(s), ester(s), salts, or anhydride(s) thereof, and more preferably the functionalized compound comprises FDCA such as 2,5-FDCA. The process may further comprise contacting the bis(2-hydroxyalkyl) (2,2'-bifuran)-5,5'-dicarboxylate, preferably bis(2-hydroxyethyl) (2,2'-bifuran)-5,5'-dicarboxylate, with the functionalized compound, preferably FDCA such as 2,5-FDCA, and forming the polyester, preferably poly(bis (2-hydroxyethyl)(2,2 '-bifuran)-5,5'-dic arboxylate-co-furandicarboxyl ate), more preferably poly [bis (2-hydroxyethyl) (2,2 '-bifuran)-5, 5'-dic arboxylate-co-2,5-furandicarboxylate].

In the preparation of polyesters according to the present invention, the polycarboxylic acid residues, e.g., the dicarboxylate structural units, may be derived from a polyfunctional acid monomer or an ester producing equivalent thereof, which may preferably include or further include the bifuran diacids described herein. Specific representative examples in addition to the bifuran diacids described herein, may be derived from oxalic acid, malonic acid, succinic acid, glutaric acid, 2-methylglutaric acid, 3-methylglutaric acid, α-ketoglutaric acid, adipic acid, pimelic acid, azelaic acid, sebacic acid, brassylic acid, fumaric acid, 2,2-dimethylglutaric acid, suberic acid, diglycolic acid, oxaloacetic acid, glutamic acid, aspartic acid, itaconic acid, maleic acid, furandicarboxylic acid (FDCA) and the isomers thereof such as 2,4-FDCA, 2,5-FDCA, and 3,4-FDCA, and so on. Biphenyldicarboxylic acids, phenylcyclohexyldicarboxylic acids, dicyclohexyldicarboxylic acids, as well as the other polycarboxylic acid compounds disclosed in WO 2015/112252 Al, and combinations thereof, may also be suitable.

The polycarboxylic acids residues are preferably biodegradable, such as those derived from the bifuran dicarboxylic acids disclosed herein, and also including those derived from other hetero and heterocyclic polycarboxylic acids such as polycarboxyls having an oxo ring including, for example, furan polycarboxyls such as the PDCAs, and the like.

The polycarboxylic acid compounds disclosed herein may be used in the diacid component in any combination, preferably in a combination including at least one (2,2'-bifuran)-5,5'-dicarboxylic acid or ester producing equivalent thereof.

In the polyesters according to the present invention, the polyhydroxyl residues, e.g., the diol structural units, may be derived from a dihydroxy compound selected from branched or linear $C_2$ to $C_{20}$ alkylene diols, preferably $C_2$ to $C_{12}$ alkylene diols, e.g., ethylene glycol, 1,2-propanediol, 1,3-propanediol, 1,2-butanediol, 1,4-butanediol, 1,5-pentanediol, 2,4-dimethyl-2-ethylhexane-1,3-diol, 2,2-dimethyl- 1,3-prop anediol (NPG), 2-ethyl-2-butyl-1,3-propanediol, 2-ethyl-2-isobutyl-1,3-propanediol, 2,2,4-trimethyl-1,6-hexanediol, and in particular ethylene glycol, 1,3-propanediol, 1,4-butanediol, and 2,2-dimethyl-1,3-propanediol (neopentyl glycol); and from alicyclic diols, preferably cyclopentanediol, 1,4-cyclohexanediol, 1,2-cyclohexanedimethanol, 1,3-cyclohexanedimethanol, 1,4-cyclohexanedimethanol, 2,2,4,4-tetramethyl-1,3-cyc lobutanediol; or any combination thereof. Biphenyldialcohols, phenylcyclohexyldialcohols, dicyclohexyldialcohols, as well as the other polyhydroxyl compounds disclosed in WO 2015/112252 A1, and combinations thereof, may also be suitable.

The polyhdroxyl residues are preferably biodegradable, such as those derived from the alkylene diols mentioned above, and also including those derived from hetero and heterocyclic polyhydroxyl hydrocarbons such as polyhydroxyls having an oxo ring including, for example, furan polyhydroxyls such as the furan diols oxolan-3,4-diol, 2,5-bis(hydroxymethyl)furan, 2,3-furandiol, tetrahydro-3,4-furandiol, and the like.

In any embodiment of the invention, the polyesters may be prepared by solution, interfacial, and/or melt polymerization techniques, including transesterification and/or polycondensation, in batch, semi-batch or continuous processes. In any embodiment of the invention, polyesterification processes may comprise contacting the respective acid and diol components, including any bifuran acid and/or diol components, together with any branching agent and/or any chain extender at polyesterification conditions, e.g., melt phase reaction at a temperature of 100° C. to 315° C. and at an absolute pressure of 0.1 to 760 mm Hg for a time sufficient to form a polyester. The polyesters are preferably prepared in a reactor equipped with a stirrer, an inert gas (e.g., nitrogen) inlet, a thermocouple, a distillation column connected to a water-cooled condenser, a water separator, and a vacuum connection tube. Any of the equipment and procedures disclosed in U.S. Pat. Nos. 4,093,603 and 5,681,918, may be adapted for implementation herein.

Polyesterification may be conducted with the introduction of an inert gas stream, such as nitrogen, to shift the equilibrium and advance to high molecular weight and/or vacuum melt phase polycondensation, preferably at temperatures above 150° C. and pressures below 130 Pa (1 mm Hg). A suitable process may gradually increase temperature, e.g., from 130° C. in the initial reaction steps up to 190 to 280° C. in the later steps, initially under normal pressure, then, when necessary, under reduced pressure at the end of each step, while maintaining these operating conditions until a polyester with the desired properties is obtained. If desired, the degree of esterification may be monitored by measuring the amount of water formed and the properties of the polyester, for example, viscosity, hydroxyl number, acid number, and so on.

The esterification conditions can preferably include an esterification catalyst, such as, for example, sulfuric acid, a sulfonic acid, and so on, preferably in an amount from 0.05 to 1.50 percent by weight of the reactants. Suitable catalysts may also include those disclosed in U.S. Pat. Nos. 4,025, 492, 4,136,089, 4,176,224, 4,238,593, and 4,208,527. Suitable catalyst systems may include compounds of Ti, Ti/P, Mn/Ti/Co/P, Mn/Ti/P, Zn/Ti/Co/P, Zn/Al, Sb (e.g., $Sb_2O_3$), Sn (e.g., dibutyltin oxide, dibutyltin dilaurate, n-butyltin trioctoate) and so on.

The esterification conditions can preferably further include optional stabilizers, such as, for example, phenolic antioxidants such as Irganoxj™ 1010 or phosphonite- and phosphite-type stabilizers such as tributylphosphite, preferably in an amount from 0 to 1 percent by weight of the reactants. When cobalt is not used in the polycondensation, copolymerizable toners may be incorporated into the copolyesters to control the color of the polyesters so that they are suitable for the intended applications where color may be an important property. In addition to the catalysts and toners, other additives, such as antioxidants, dyes, etc., may be used during the polyesterification, or may be added after formation of the polymer.

The polymerization may optionally include a solid-state polymerization (SSP) stage, following the melt phase, under conditions effective to increase the molecular weight. SSP may comprise grinding the solid polymer (after cooling) following the melt phase polymerization, optionally annealing the ground polymer, and heating the ground polymer to polymerization temperature. If used, the annealing temperature is preferably above 100° C., or above 120° C., or above 140° C., e.g., 160° C. The SSP reaction temperature is preferably greater than 200° C., e.g., 210-220° C., under vacuum for a sufficient period of time to increase the molecular weight, preferably increasing the inherent viscosity by at least 10%.

In any embodiment, the polyesters may include conventional additives including pigments, colorants, stabilizers, antioxidants, extrusion aids, reheat agents, slip agents, carbon black, flame retardants and mixtures thereof. In any embodiment, the polyester may be combined or blended with one or more modifiers and/or blend polymers including polyamides; e.g., Nylon™ 6,6 (DuPont), poly(ether-imides), polyphenylene oxides, e.g., poly(2,6- to dimethylphenylene oxide), poly(phenylene oxide)/polystyrene blends; e.g., Noryl™ (GE), other polyesters, polyphenylene sulfides, polyphenylene sulfide/sulfones, poly(ester-carbonates), polycarbonates; e.g., Lexan™ (GE), polysulfones, polysulfone ethers, poly(ether-ketones), combinations thereof, and the like.

Any of the polyesters described herein may be melt processed, e.g., for the preparation of molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art. Accordingly, composites according to the instant invention can be extruded and/or molded using conventional melt processing techniques to produce a shaped article.

EXAMPLES

Example 1

Polymerization of Coupled Product and furan dicarboxylic Acids

Examples are shown in Schemes 2 and 2A for the polymerization of coupled furans beginning with the formation of furan-2-carbaldehyde from biomass. In Scheme 2 the furan-2-carbaldehyde is protected with ethylene glycol and coupled, e.g., via electropalladation. The coupled furan can be deprotected to obtain the corresponding (2,2'-bifuran)-5,5'-dicarbaldehyde, and the ethylene glycol recycled to the protection step; or, the coupled furan can be polymerized with a dicarboxylic acid such as furan-2,5-dicarboxylic acid.

Scheme 2

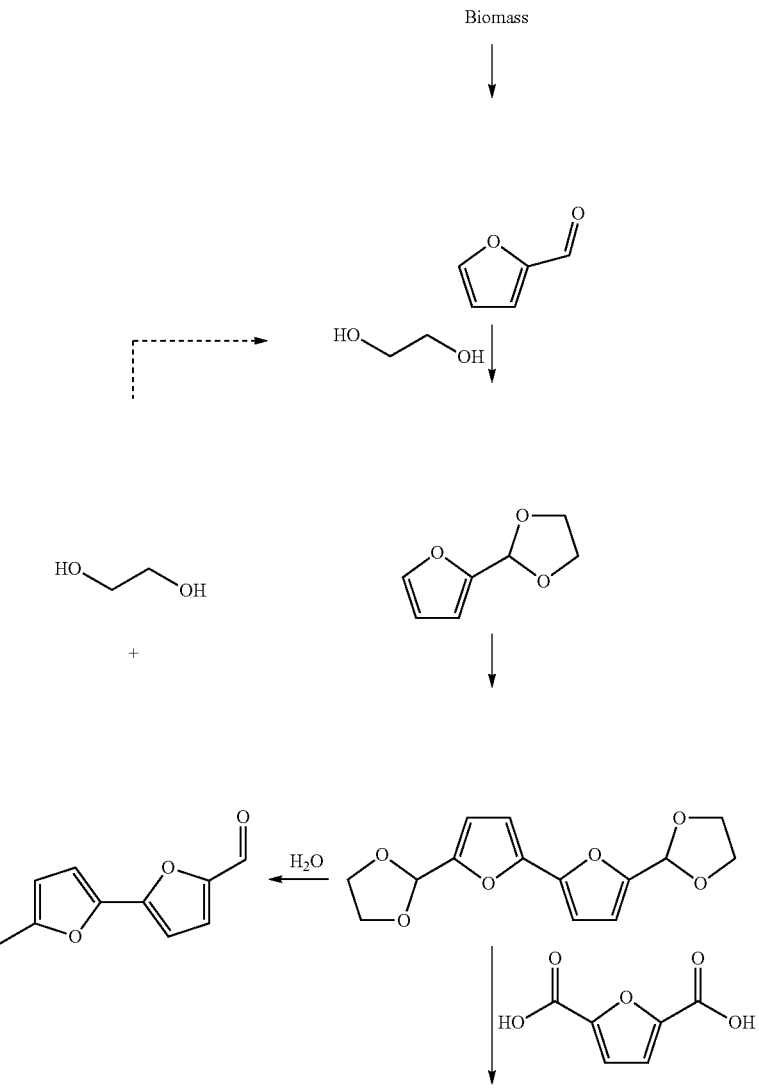

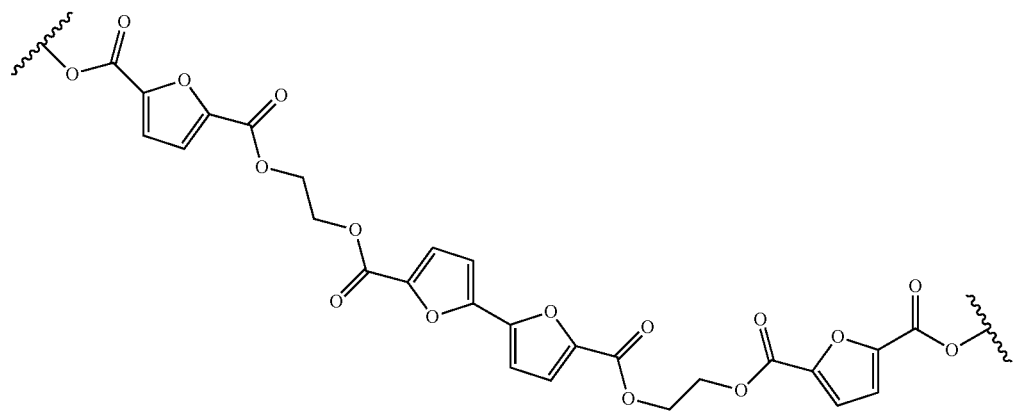

Renewable Block Polymer

Other di-acids, or di-esters, from renewable or non-renewable sources, can also be used as the linking agent for the polyester. Examples of such di-acids/di-esters are: terephthalic acid, dimethyl terephthalate, succinic acid, adipic acid, or oxalic acid. The reaction conditions can be tuned to favor the alternating copolymer over a random copolymer. In Scheme 2A, the protected bifuran is polymerized directly, with recycle of released glycol to the furaldehyde protection step.

Scheme 2A

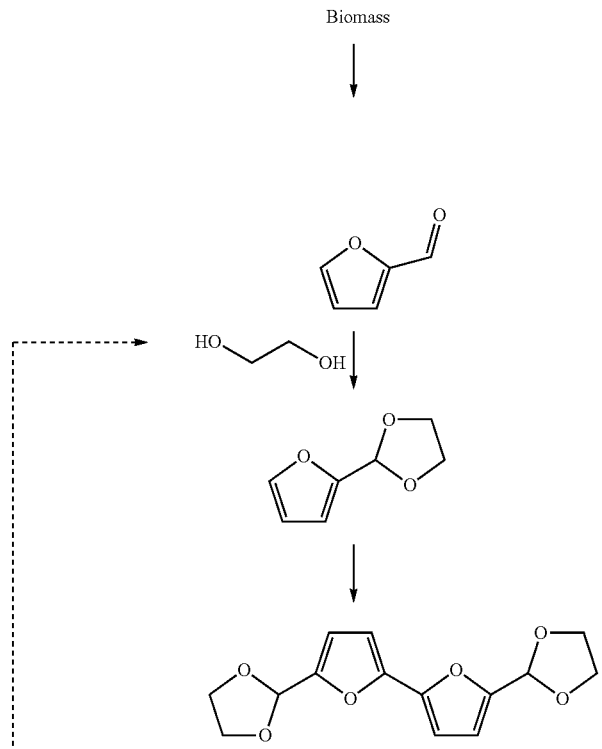

-continued

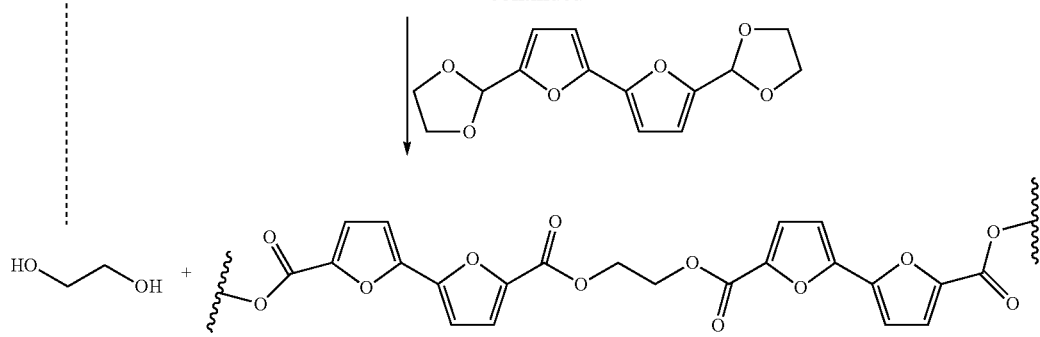

Example 2

Protecting Carbonyl in furfural with ethylene glycol

A mixture of furfural (96.1 mg, 1.0 mmol), ethylene glycol (124.1 mg, 2.0 mmol) and montmorillonite K-10 (300 mg) in toluene (20 mL) was stirred at reflux for 2 hours using a Dean-Stark apparatus to remove water. After cooling, the catalyst was removed by filtration and the solvent was evaporated under reduced pressure to give product (138.7 mg, 99%) as a light oil. $^1$H NMR matched commercially obtained 2-furfural ethylene glycol acetal.

Example 3

Coupling 2-furfural ethylene glycol acetal

A 40-mL reaction vial was charged with palladium(II) acetate (157 mg, 0.7 mmol), acetonitrile (15 mL), and 2-(1,3-dioxolan-2-yl)furan (981 mg, 7 mmol). The reaction vial was sealed with an air atmosphere and the reaction stirred for 24 h at 82° C. The reaction mixture was filtered then subjected to $^1$H NMR and it was determined that 5,5'-di(ethylene glycol acetal)-2,2'-bifuran was formed in ~15% yield (integration). To further confirm, 1 mL of 1M aqueous HCl was added to the reaction mixture to de-protect any carbonyls. $^1$H NMR confirmed the presence of [2,2'-bifuran]-5,5'-dicarbaldehyde by comparing it to literature values (Itahara, Toshio in Synthesis 255-256 (1984))

Example 4

Polymerization of 5,5'-di(ethylene glycol acetal)-2,2'-bifuran and furan dicarboxylate Scheme 3 shows a pathway comprising oxidation and hydrolysis of 5,5'-di(ethylene glycol acetal)-2,2'-bifuran to form the intermediate bis(2-hydroxyethyl) (2,2'-bifuran)-5,5'-dicarboxylate, and esterification with 2,5-furan dicarboxylic acid or dimethyl 2,5-furandicarboxylate (not shown).

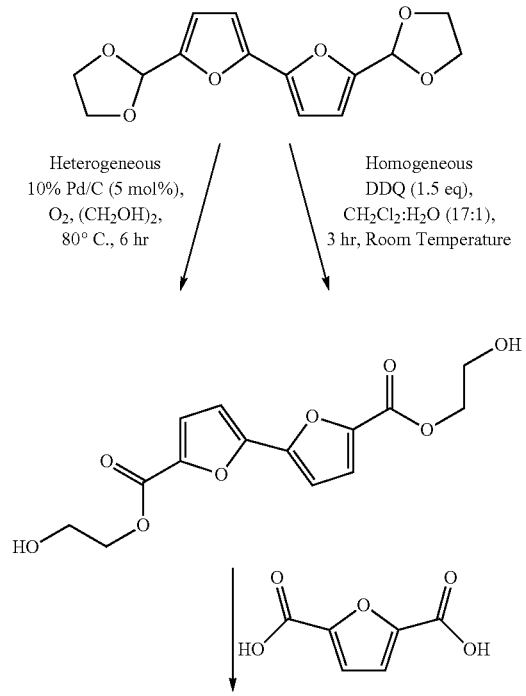

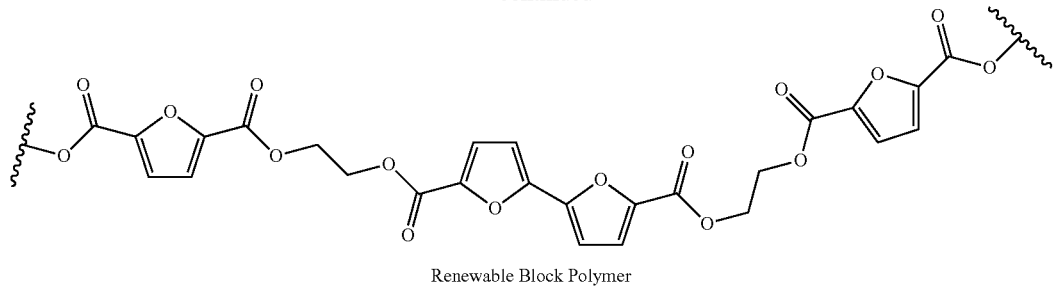

Renewable Block Polymer

The oxidation and hydrolysis are effected homogenously using 2,3-dichloro-5,6-dicyano-1,4-benzoquinone (DDQ, 1.5 equivalents) in a solution of dichloromethane and water (17:1 $CH_2Cl_2:H_2O$) at room temperature for 3 hours, or heterogeneously using 10 wt % palladium on carbon (5 mol % Pd) in methanediol in the presence of an oxidant such as, for example, oxygen at 80° C. for 6 h. Either the furan diester or the dicarboxylic acid is used in the esterification. This example minimizes or essentially prevents the formation of the homopolymer of the bifuran diacid, and selectivity is facilitated since the bifuran is already functionalized with hydroxyethyl carboxylate.

Example 5

Conversion of 2,2'-bifuran-5,5'-di(ethylene glycol acetal) to dimethyl (2,2'-bifuran)-5,5'-dicarboxylate 2-Furfural ethylene glycol acetal is converted to the methyl ester in high yield using a procedure analogous to that described for the uncoupled furan in Patel, Bhisma K. et al. in 43 *Tet. Lett.* 5123-5126 (2002). The technique is illustrated in Scheme 4 using a catalytic quantity of vanadium pentoxide/hydrogen peroxide in methanol.

Scheme 4

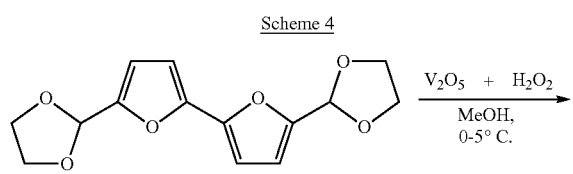

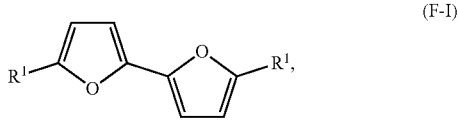

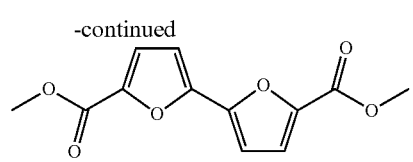

The dicarboxylate ester is then reacted with a diol (not shown) to form the corresponding polyester.

Example 6

Polymerization of ethylene glycol and 2,2'-bifuran-5,5'-di(ethylene glycol acetal) to polyester If the methanol in Example 5 is replaced with a diol, e.g., ethylene glycol, in excess, the polyester is formed directly, according to Scheme 5.

Scheme 5

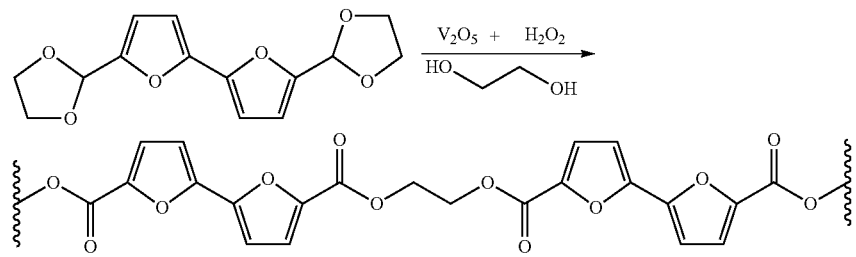

Having described all the features of the bifuran and the process of making such compounds, described here in numbered paragraphs is:

P1. A composition of matter comprising 5,5'-di-(protected)-2,2'-bifuran having the Formula (F-I) or preferably Formula (F-II), wherein Formula (F-I) is:

(F-I)

wherein each IV is independently a 5- or 6-member 1,3-dioxo-2-yl ring radical, which may optionally be substituted with one or more substituents preferably comprising alkyl radical(s) having from 1 to 12 carbon atoms, more preferably each IV is 1,3-dioxolan-2-yl or 1,3-dioxan-2-yl; and wherein Formula (F-II) is:

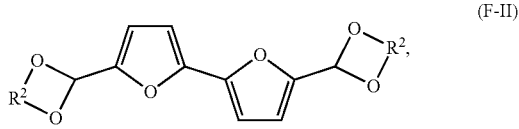

(F-II)

wherein each $R^2$ is independently an alkylene of from 2 to 12 carbon atoms; preferably 1,2-ethylene or 1,3-propylene or substituted 1,2-ethylene or 1,3-propylene, wherein the substituents are selected from alkyls of 1 to 10 carbon atoms; more preferably each $R^2$ is independently 1,2-ethylene, 1,2-propylene, or 1,3-propylene; more preferably ethylene, i.e., wherein the 5,5'-di-(protected)-2,2'-bifuran is 5,5'-di-(1,3-dioxolan-2-yl)-2,2'-bifuran.

P2. A furan coupling process comprising coupling a protected 2-furaldehyde to form a 5,5'-di-(protected)-2,2'-bifuran.

P3. The process of numbered paragraph 2, wherein the coupling comprises oxidative addition, metalation, and reductive elimination, optionally in the presence of an oxidant and/or a catalyst.

P4. The process of numbered paragraph 2 or numbered paragraph 3, wherein the coupling comprises palladation, preferably electrophilic palladation, preferably in the presence of an oxidant (preferably oxygen) and a palladium catalyst, preferably a palladium (II) catalyst such as $PdCl_2$, $PdBr_2$, PdO, $Pd(CN)_2$, $Pd(NO_3)_2$, Pd(II) carboxylate salts, more preferably Pd(II) halocarboxylate salts, or more preferably palladium (II) acetate ($Pd(OAc)_2$) and/or palladium (II) trifluoroacetate ($Pd(OOCCF_3)_2$), or any combination thereof.

P5. The process of any of numbered paragraphs 2 to 4, further comprising protecting 2-furaldehyde to form the protected 2-furaldehyde.

P6. The process of numbered paragraph 5, wherein the 2-furaldehyde is protected by reacting with an alkylene diol to form a 2-furfural alkylene diol acetal.

P7. The process of numbered paragraph 6, wherein the alkylene diol comprises from 2 to 12 carbon atoms, preferably the alkylene diol comprises ethylene glycol.

P8. The process of any of numbered paragraphs 5 to 7, wherein the protection is in the presence of a catalyst, preferably a Brønsted and/or Lewis acid, preferably an inorganic oxide, preferably oxides of metals and metalloids from Group 14, 13, 4, and 2 of the Periodic Table of the elements, preferably silicon, aluminum, magnesium, and/or zirconium oxides, more preferably a silicate, more preferably a phyllosilicate, more preferably a clay mineral, more preferably montmorillonite, more preferably montmorillonite K-10, preferably with water removal, and optionally in the presence of a solvent, preferably toluene.

P9. The process of any of numbered paragraphs 2 to 8, further comprising deprotecting the 5,5'-di(protected)-2,2'-bifuran to form (2,2'-bifuran)-5,5'-dicarbaldehyde.

P10. The process of numbered paragraph 9, wherein the 5,5'-di(protected)-2,2'-bifuran comprises 5,5'-di(alkylene diol acetal)-2,2'-bifuran, preferably 5,5'-di(alkylene diol acetal)-2,2'-bifuran, more preferably 5,5'-di(ethylene glycol acetal)-2,2'-bifuran.

P11. The process of numbered paragraph 9 or numbered paragraph 10, wherein the deprotecting comprises contacting the 5,5'-di(protected)-2,2'-bifuran with catalyst, preferably a Brønsted and/or Lewis acid, preferably in an acidic aqueous medium, preferably aqueous HCl.

P12. A process comprising polymerizing a 5,5'-di(protected)-2,2'-bifuran in one or more steps, optionally including formation of one or more intermediate 5,5'-di-(substituted)-2,2'-bifurans, to form a polyester comprising (2,2'-bifuran)-5,5'-dicarboxylate structural units, preferably wherein the polyester comprises poly(alkylene glycol (2,2'-bifuran)-5,5'-dicarboxylate) structural units, more preferably poly(ethylene glycol (2,2'-bifuran)-5,5'-dicarboxylate) structural units.

P13. The process of any of numbered paragraphs 2 to 11, further comprising polymerizing the 5,5'-di(protected)-2,2'-bifuran in one or more steps, optionally including formation of one or more intermediate 5,5'-di-(substituted)-2,2'-bifurans, to form a polyester comprising (2,2'-bifuran)-5,5'-dicarboxylate structural units, preferably wherein the polyester comprises poly(alkylene glycol (2,2'-bifuran)-5,5'-dicarboxylate) structural units, more preferably poly(ethylene glycol (2,2'-bifuran)-5,5'-dicarboxylate) structural units.

P14. The process of numbered paragraph 12 or numbered paragraph 13, further comprising reacting the 5,5'-di(protected)-2,2'-bifuran and forming at least one intermediate, preferably wherein the at least one intermediate comprises a 5,5'-di-(substituted)-2,2'-bifuran wherein the 5,5' substituents comprise hydroxyl groups, carboxylic acid groups, ester producing equivalents thereof (preferably the corresponding acid halide(s), ester(s), salts, or anhydride(s) thereof), or a combination thereof; optionally recovering the intermediate (s);

and polymerizing an ultimate one of the intermediate(s), preferably by contacting the 5,5'-di-(substituted)-2,2'-bifuran with a functionalized compound comprising two or more ester-forming functional groups, to form a polyester, preferably wherein the hydrocarbyl comprises a heterocyclic group, more preferably the hydrocarbyl comprises an oxo ring, preferably an unsaturated oxo ring, more preferably furanyl or pyranyl.

P15. The process of numbered paragraph 14, wherein the ultimate intermediate has the following Formula (F-III):

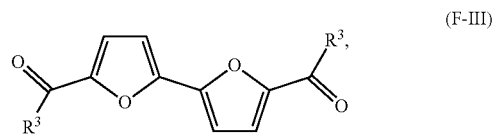

(F-III)

wherein each $R^3$ is independently hydrogen, hydroxyalkyl, carboxyalkyl, halide, OR', or a combination thereof, or wherein the ultimate intermediate is an anhydride thereof, where R' (if present) is hydrogen, hydrocarbyl, hydroxyalkyl, carboxyalkyl, or a combination thereof, preferably wherein $R^3$ and R' (if present) have a number of carbon atoms equal to or less than 20, more preferably equal to or less than 10, more preferably where R' is methyl.

P16. The process of numbered paragraph 14 or numbered paragraph 15, further comprising protecting 2-furaldehyde with an alkylene diol to form a 2-furfural alkylene diol acetal; wherein forming the at least one intermediate comprises producing alkylene diol; and optionally recycling the alkylene diol from the at least one intermediate formation step to the 2-furaldehyde protection step.

P17. The process of any of numbered paragraphs 14 to 16, wherein a first one of the intermediates comprises (2,2'-bifuran)-5,5'-dicarbaldehyde.

P18. The process of numbered paragraph 17, further comprising converting the (2,2'-bifuran)-5,5'-dicarbaldehyde to (2,2'-bifuran)-5,5'-dicarboxylic acid or dialkyl (2,2'-bifuran)-5,5'-dicarboxylate (preferably dimethyl (2,2'-bifuran)-5,5'-dicarboxylate), or a combination thereof.

P19. The process of numbered paragraph 18, wherein the conversion comprises heating the (2,2'-bifuran)-5,5'-dicarbaldehyde in the presence of an oxidant, preferably oxygen, preferably to a temperature of 100-200° C., preferably in a solvent (preferably acetic acid), preferably at an absolute pressure from 100 kilopascal to 6,000 kilopascal, preferably wherein the 5,5'-di-(substituted)-2,2'-bifuran comprises (2,2'-bifuran)-5,5'-dicarboxylic acid.

P20. The process of numbered paragraph 18, wherein the conversion comprises contacting the (2,2'-bifuran)-5,5'-dicarbaldehyde in the presence of an oxidant, preferably oxygen with a metal or metalloid catalyst, preferably Pd, Pb, Mg, or a combination thereof, preferably at a temperature from 40 to 160° C. (more preferably around 80° C. ±15, 10, or 5° C.), preferably at an absolute pressure from 100 kilopascal to 2,000 kilopascal (more preferably around 500 kilopascal ±200 or ±100 kilopascal), preferably wherein the 5,5'-di-3 0 (substituted)-2,2'-bifuran comprises dialkyl (2,2'-bifuran)-5,5'-dicarboxylate, preferably dimethyl (2,2'-bifuran)-5,5'-dicarboxylate.

P21. The process of any of numbered paragraphs 14 to 20, wherein the ultimate intermediate 5,5'-di-(substituted)-2,2'-bifuran has the Formula (F-IV):

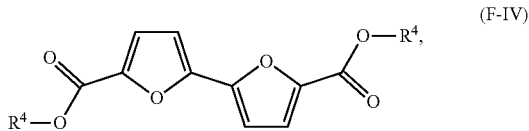

(F-IV)

wherein each $R^4$ is hydrogen, hydrocarbyl, hydroxyalkyl, carboxyalkyl, or a combination thereof, or wherein the ultimate intermediate is an anhydride thereof, preferably wherein each $R^4$ has a number of carbon atoms equal to or less than 20, more preferably equal to or less than 10, more preferably where each $R^4$ is hydrogen, methyl, hydroxyethyl, or a combination thereof.

P22. The process of numbered paragraph 21, wherein the 5,5'-di(protected)-2,2'-bifuran comprises 5,5'-di-(alkylene diol acetal)-2,2'-bifuran, and formation of the intermediate comprises contacting the 5,5'-di-(alkylene diol acetal)-2,2'-bifuran with vanadium (V) oxide and peroxide, preferably hydrogen peroxide, preferably at a temperature less than 20° C., preferably at 0-15° C., preferably in an alcoholic medium, more preferably in methanol, and wherein R is alkyl, preferably methyl.

P23. The process of any of numbered paragraphs 14 to 22, wherein the 5,5' substituents of the ultimate intermediate 2,2'-bifuran comprise carboxylic acid groups or ester producing equivalents thereof (preferably the corresponding acid halide(s), ester(s), salts, or anhydride(s) thereof), preferably the 5,5'-di-(substituted)-2,2'-bifuran compound comprises (2,2'-bifuran)-5,5'-dicarboxylic acid, dialkyl (2,2'-bifuran)-5,5'-dicarboxylate (preferably dimethyl (2,2'-bifuran)-5,5'-dicarboxylate), or a combination thereof; and wherein the polymerization comprises contacting the ultimate intermediate with the functionalized compound and forming the polyester, wherein the functionalized compound comprises two or more hydroxyl groups, preferably alkylene diol, more preferably ethylene glycol.

P24. The process of any of numbered paragraphs 12 to 16, wherein the 5,5'-di(protected)-2,2'-bifuran comprises 5,5'-di-(alkylene diol acetal)-2,2'-bifuran, and formation of the intermediate comprises contacting the 5,5'-di-(alkylene diol acetal)-2,2'-bifuran with palladium on carbon catalyst (preferably 5 mole percent Pd on carbon) in the presence of an oxidant, preferably oxygen, preferably at a temperature from 40 to 160° C., preferably at 80° C. ±20° C., preferably in methanediol, to form bis(2-hydroxyalkyl) (2,2'-bifuran)-5,5'-dicarboxylate, preferably bis(2-hydroxyethyl) (2,2'-bifuran)-5,5'-dicarboxylate.

P25. The process of numbered paragraph 24, wherein the functionalized compound comprises two or more carboxylic acid groups or ester producing equivalents thereof (preferably the corresponding acid halide(s), ester(s), salts, or anhydride(s) thereof), preferably the functionalized compound comprises 2,5-furandicarboxylic acid; the process further comprising: contacting the bis(2-hydroxyalkyl) (2,2'-bifuran)-5,5'-dicarboxylate, preferably bis(2-hydroxyethyl) (2,2'-bifuran)-5,5'-dicarboxylate, with the functionalized compound, preferably 2,5-furandicarboxylic acid, and forming the polyester, preferably poly(bi s (2-hydroxyethyl) (2,2'-bifuran)-5,5'-dic arboxylate-co-2,5-furandic arboxyl ate).

Although only a few example embodiments have been described in detail above, those skilled in the art will readily appreciate that many modifications are possible in the example embodiments without materially departing from this invention. Accordingly, all such modifications are intended to be included within the scope of this invention as defined in the following claims.

The invention claimed is:

1. A furan coupling process comprising coupling a protected 2-furaldehyde to form a 5,5'-di-(protected)-2,2'-bifuran.

2. The process of claim 1, wherein the coupling comprises oxidative addition, metalation, and reductive elimination, optionally in the presence of an oxidant and/or a catalyst.

3. The process of claim 1, wherein the coupling comprises palladation.

4. The process of claim 1, further comprising protecting 2-furaldehyde to form the protected 2-furaldehyde.

5. The process of claim 4, wherein the 2-furaldehyde is protected by reacting with an alkylene diol to form a 2-furfural alkylene diol acetal.

6. The process of claim 5, wherein the alkylene diol comprises from 2 to 12 carbon atoms.

7. The process of claim 4, wherein the protection is in the presence of a catalyst.

8. The process of claim 1, further comprising deprotecting the 5,5'-di(protected)-2,2'-bifuran to form (2,2'-bifuran)-5,5'-dicarbaldehyde.

9. The process of claim 8, wherein the 5,5'-di(protected)-2,2'-bifuran comprises 5,5'-di(alkylene diol acetal)-2,2'-bifuran.

10. The process of claim 8, wherein the deprotecting comprises contacting the 5,5'-di(protected)-2,2'-bifuran with catalyst.

11. The process of claim 1, further polymerizing a 5,5'-di(protected)-2,2'-bifuran in one or more steps, optionally including formation of one or more intermediate 5,5'-di-(substituted)-2,2'-bifurans, to form a polyester comprising (2,2'-bifuran)-5,5'-dicarboxylate structural units.

12. The process of claim 1, further comprising polymerizing the 5,5'-di(protected)-2,2'-bifuran in one or more steps, optionally including formation of one or more intermediate 5,5'-di-(substituted)-2,2'-bifurans, to form a polyester comprising (2,2'-bifuran)-5,5'-dicarboxylate structural units.

13. The process of claim 11, further comprising:
reacting the 5,5'-di(protected)-2,2'-bifuran and forming at least one intermediate;
optionally recovering the intermediate(s); and
polymerizing an ultimate one of the intermediate(s).

14. The process of claim 13, wherein the ultimate intermediate has the following Formula (F-III):

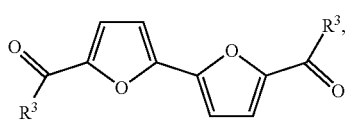

(F-III)

wherein each $R^3$ is independently hydrogen, hydroxyalkyl, carboxyalkyl, halide, OR', or a combination thereof, or
wherein the ultimate intermediate is an anhydride thereof, where R' (if present) is hydrogen, hydrocarbyl, hydroxyalkyl, carboxyalkyl, or a combination thereof.

15. The process of claim 13, further comprising protecting 2-furaldehyde with an alkylene diol to form a 2-furfural alkylene diol acetal; wherein forming the at least one intermediate comprises producing alkylene diol; and optionally recycling the alkylene diol from the at least one intermediate formation step to the 2-furaldehyde protection step.

16. The process of claim 13, wherein a first one of the intermediates comprises (2,2'-bifuran)-5,5'-dicarbaldehyde.

17. The process of claim 16, further comprising converting the (2,2'-bifuran)-5,5'-dicarbaldehyde to (2,2'-bifuran)-5,5'-dicarboxylic acid or dialkyl (2,2'-bifuran)-5,5'-dicarboxylate, or a combination thereof.

18. The process of claim 17, wherein the conversion comprises heating the (2,2'-bifuran)-5,5'-dicarbaldehyde in the presence of an oxidant.

19. The process of claim 17, wherein the conversion comprises contacting the (2,2'-bifuran)-5,5'-dicarbaldehyde in the presence of an oxidant.

20. The process of claim 13, comprising wherein the ultimate intermediate 5,5'-di-(substituted)-2,2'-bifuran has the Formula (F-IV):

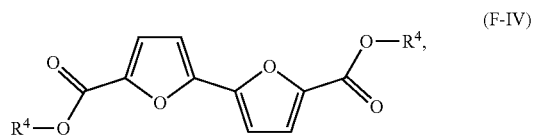

(F-IV)

wherein each $R^4$ is hydrogen, hydrocarbyl, hydroxyalkyl, carboxyalkyl, or a combination thereof, or wherein the ultimate intermediate is an anhydride thereof.

21. The process of claim 20, wherein the 5,5'-di(protected)-2,2'-bifuran comprises 5,5'-di-(alkylene diol acetal)-2,2'-bifuran, and formation of the intermediate comprises contacting the 5,5'-di-(alkylene diol acetal)-2,2'-bifuran with vanadium (V) oxide and peroxide.

22. The process of claim 13, wherein the 5,5' substituents of the ultimate intermediate 2,2'-bifuran comprise carboxylic acid groups or ester producing equivalents thereof; and
wherein the polymerization comprises contacting the ultimate intermediate with the functionalized compound and forming the polyester, wherein the functionalized compound comprises two or more hydroxyl groups.

23. The process of claim 11, wherein the 5,5'-di(protected)-2,2'-bifuran comprises 5,5'-di-(alkylene diol acetal)-2,2'-bifuran, and formation of the intermediate comprises contacting the 5,5'-di-(alkylene diol acetal)-2,2'-bifuran with palladium on carbon catalyst in the presence of an oxidant.

24. The process of claim 23, wherein the functionalized compound comprises two or more carboxylic acid groups or ester producing equivalents thereof; the process further comprising contacting the bis(2-hydroxyalkyl) (2,2'-bifuran)-5,5'-dicarboxylate, with the functionalized compound.

* * * * *